United States Patent [19]
Calari

[11] 4,180,460
[45] Dec. 25, 1979

[54] PORTABLE MACHINE FOR REGENERATIVE DIALYSIS

[75] Inventor: Alessandro Calari, Mirandola, Italy

[73] Assignee: Bellco S.p.A., Mirandola, Italy

[21] Appl. No.: 968,586

[22] Filed: Dec. 11, 1978

[30] Foreign Application Priority Data

Jan. 20, 1978 [IT] Italy ............... 19480 A/78

[51] Int. Cl.² .................... B01D 13/00; B01D 31/00
[52] U.S. Cl. .................. 210/182; 210/196; 210/253; 210/257.2; 210/258; 210/259; 210/266; 210/295; 210/321 B
[58] Field of Search ............ 210/321 A, 321 B, 27, 210/175, 181, 184, 186, 195 R, 196, 182, 253, 257 M, 258, 259, 266, 295, 24 R, 34, 40, 74, 433 M, 434, 167, 85; 219/300, 308, 328, 331, 497; 237/8 A; 73/1 F; 343 B; 128/DIG. 3

[56] References Cited

U.S. PATENT DOCUMENTS

| | | | |
|---|---|---|---|
| 2,218,868 | 10/1940 | Bichon | 219/300 |
| 2,478,917 | 8/1949 | Hain | 219/300 |
| 3,099,737 | 7/1963 | Naxon | 219/38 |
| 3,506,126 | 4/1970 | Serfass et al. | 210/96 |
| 3,582,968 | 6/1971 | Buiting et al. | 219/300 |
| 3,669,880 | 6/1972 | Marantz et al. | 210/22 |
| 3,878,095 | 4/1975 | Frasier et al. | 210/87 |
| 3,958,555 | 5/1976 | Horne | 126/362 |
| 3,979,284 | 9/1976 | Granger et al. | 210/22 A |
| 4,118,314 | 10/1978 | Yoshida | 210/22 C |

Primary Examiner—Charles N. Hart
Assistant Examiner—David R. Sadowski
Attorney, Agent, or Firm—Guido Modiano; Albert Josif

[57] ABSTRACT

A portable machine for regenerative dialysis comprises a dialyzing liquid reservoir in which is immersed a suction duct connected to a heating tube the temperature of which is controlled by a thermal probe pair piloting a temperature adjusting element. The outlet of the heating tube is connected to the suction side of a dialyzing liquid pump having a first and second delivery ducts opening in the dialyzing liquid reservoir wherein are interposed a dialyzer element and a dialyzing liquid regenerating cartridge respectively.

8 Claims, 3 Drawing Figures

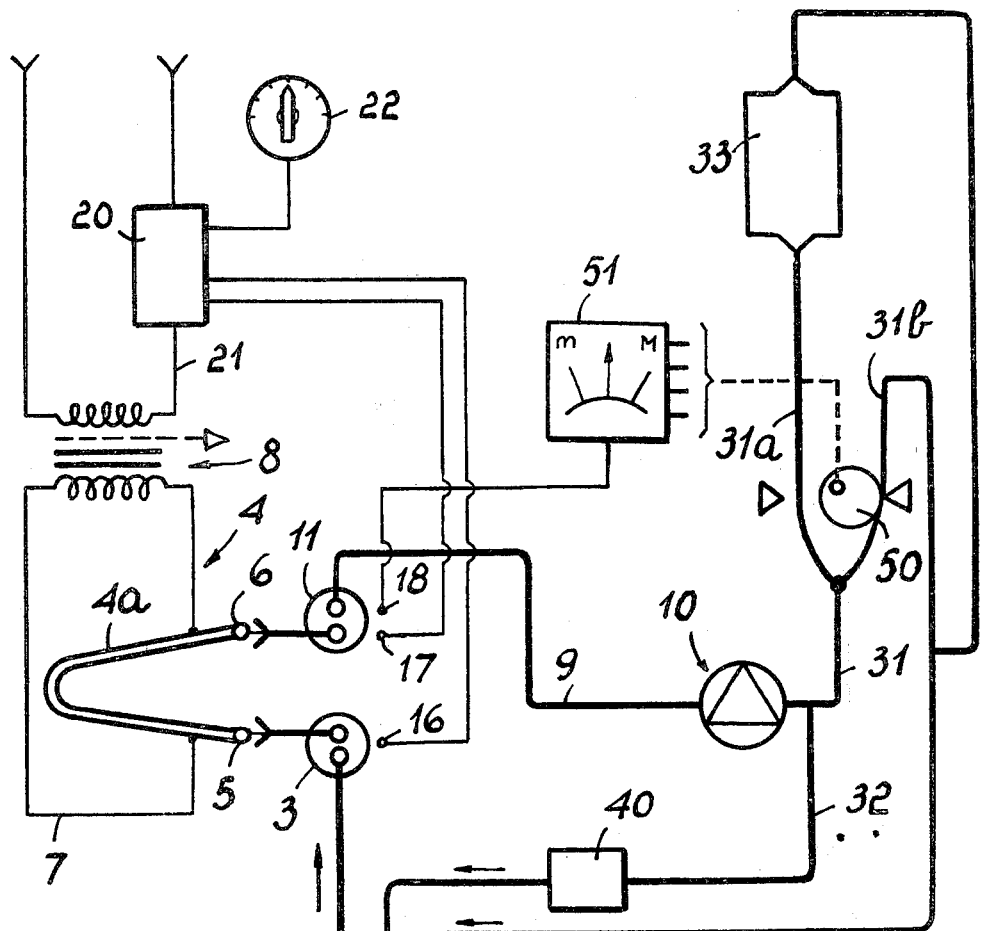
Fig.1
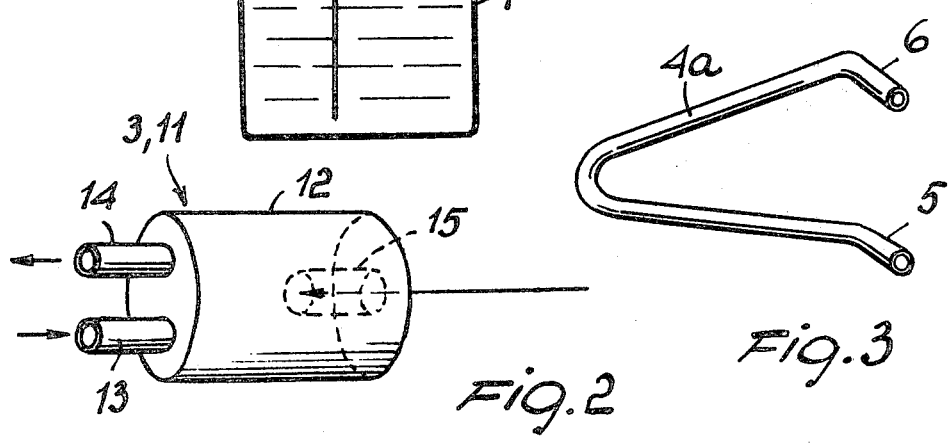
Fig.2
Fig.3

PORTABLE MACHINE FOR REGENERATIVE DIALYSIS

BACKGROUND OF THE INVENTION

This invention relates to a portable machine for regenerative dialysis.

As is known to those skilled in the art in dialysis operations, a dialyzer element is utilized which may be of several different types and configurations, wherein a path for the blood and path for the dialyzing liquid are provided, such paths being separated from each other by means of membranes of Cuprophane or Cellophane.

The dialyzing liquid serves the function of removing from the blood impurities which are, in a way, passed through the membranes mentioned above. The dialyzing liquid, after passing through the dialyzer element, is generally discarded with an obvious and significant waste, since that liquid is a fairly costly one, and moreover, still contains valuable energetic substances.

In order to eliminate the drawbacks set forth above, systems have been proposed for regenerating the dialyzing liquid, which is caused to pass through regenerative cartridges effective to remove existing impurities and replace any substance extracted.

Such a dialyzing liquid recirculating system, while acceptable in theory, has failed so far to provide the results hoped for, because of serious problems encountered in controlling the temperature of the dialyzing liquid, and because the machinery to be employed is still quite complex and expensive.

Thus, it becomes impossible to carry out in an easy and quick manner so-called "home dialyses", using conventional machines, which would represent the optimum solution for all those patients which are affected by serious kidney malfunction.

SUMMARY OF THE INVENTION

Accordingly, it is an object of this invention to provide a portable machine for regenerative dialysis, which while affording recirculation and, therefore, re-utilization of the dialyzing liquid, is also extremely simplified in construction and simple to operate.

It is another object of the invention to provide a portable machine for regenerative dialysis, which by virtue of its simple construction is specially suitable for use in so-called "home dialysis", thus meeting in a most effective manner the requirements of numerous patients affected by kidney malfunction.

It is a further object of this invention to provide a machine wherein all of the elements in the path of the dialyzing fluid are of the "throw-away" type, thereby rendering any sterilization unnecessary.

Still another object of this invention is to provide a portable machine for regenerative dialysis which affords an accurate control over temperature, as detected by means of aseptic sensors, such as to bring the dialyzing liquid to an optimal safety condition for the patient.

Yet another object of the invention is to provide a portable machine for regenerative dialysis which can be easily obtained from commonly available components, requires no special or complex maintenance, and is extremely inexpensive.

These and other objects, such as will be apparent hereinafter, are achieved by a portable machine for regenerative dialysis, characterized in that it comprises a reservoir for the dialyzing liquid, a suction duct immersed in said reservoir, a heating element connected to said suction duct, a first element sensing the temperature of the dialyzing liquid interposed between said suction duct and said heating element, a pump with the suction side thereof connected to said heating element, a second element sensing the temperature of the dialyzing liquid interposed between said pump and said heating element, a first and second delivery ducts of said pump opening into said reservoir, a dialyzer element interposed in said first delivery duct, a dialyzing liquid regenerating cartridge interposed in said second delivery duct, a first and second thermal probes respectively associated with said first and second temperature sensing elements, and a temperature adjusting member controlling said heating element and driven by said first and second thermal probes.

BRIEF DESCRIPTION OF THE DRAWING

Further features and advantages will be more clearly apparent from the description which follows of a preferred, though not exclusive, embodiment of the instant portable machine for the regenerative dialysis, illustrated by way of example and not of limitation in the accompanying drawing, where:

FIG. 1 shows schematically the functional components of the portable machine according to this invention;

FIG. 2 is a schematical perspective view showing the configuration of the temperature sensing members; and FIG. 3 is a perspective view of a heating tube making part of the heating element.

DESCRIPTION OF A PREFERRED EMBODIMENT

With reference to the cited drawing figures, the portable machine according to the invention comprises a reservoir 1 for the dialyzing liquid, which usually contains ten liters of dialyzing liquid at an initial temperature higher than, or equal to, 15° C., these values being, of course, given herein by way of example only. The reservoir 1 is equipped with a level indicator which permits evaluation of the amount of the ultra-filtered liquid.

In said reservoir 1, there is immersed the pickup end of a suction duct 2 which is connected to a heating element indicated generally at 4, with the interposition of a first sensor member 3 sensing the temperature of the dialyzing liquid, which will be described in a more detailed way hereinafter.

Said heating element comprises a heating tube 4a made of an electrically conductive material which has a substantially "V" shape and is located in a vertical plane such that its inlet end 5 is positioned at a lower level than the outlet end 6, and that an evenly and gradually rising dialyzing liquid path is defined therewithin.

Said heating tube 4a is in series relationship and electrically connected to the secondary winding 7 of an electric transformer 8, thereby the tube 4a, additionally serving as duct for the dialyzing liquid to flow therethrough, also acts as an electric resistor for heating the dialyzing liquid itself.

The outlet end 6 of the heating tube 4a is connected to the suction side 9 of a dialyzing liquid pump 10, which is generally of the peristaltic type.

At said outlet end of the heating tube 4a on the suction side 9, a second temperature sensing member 11 is arranged which has the function of controlling the temperature of the dialyzing liquid at the outlet of the heating tube 4a.

Said first and second temperature sensor members 3 and 11 comprise a cylindrical cell 12 (FIG. 2), which is provided at one base thereof with an inlet port 13 and outlet port 14, located diametrically opposite each other and so positioned as to have the inlet port 13 below the outlet port 14, the cell 12 being installed in actual practice such as to have its axis extending horizontally.

On the opposite base of the cell 12 to the base having the ports 13 and 14, an outward opening cylindrical cavity 15 is defined, the function of which will be explained hereinafter.

The sensor members described hereinabove, namely the sensor member 3 and sensor member 11, are of substantially similar construction, thereby one sensor only has been described herein in detail.

To said first temperature sensor member 3, there is associated a first thermal probe 16 which can be inserted into the cavity 15, whereas to the second temperature sensor member there are respectively associated a second and third thermal probes 17 and 18, which sense, of course, that same temperature.

Said first thermal probe 16 and second thermal probe 17 drive a thermal adjusting member 20 which is connected across the primary winding 21 of said transformer 8. The thermal adjusting member 20, which is linked to a selected-temperature setting assembly 22, has the function of controlling the heating element 4, in accordance with the temperature differential of the dialyzing liquid at the inlet and outlet of the heating tube, and obviously in accordance with the selected temperature preset on the assembly 22. From said peristaltic pump 10, there extend a first delivery duct 31 and second delivery duct 32, which both open into said reservoir 1.

Said first delivery duct 31 bifurcates into a first branch 31a, whereon is inserted a dialyzer element 33, and second branch 31b bypassing said dialyzer element 33.

At said difurcation, there is provided an electric clamp 50, effective to shut off in an aseptic manner alternately the ducts 31a and 31b, which is controlled by a control unit 51 driven by said third thermal probe 18. More specifically, said electric clamp 50 shuts off one or the other of the branches in accordance with the operating conditions preset by the control unit 51. On the control unit 51, a minimum temperature and maximum temperature are preset, within which the temperature of the dialyzing liquid should fluctuate; if the temperature of the dialyzing liquid falls out of the preset range, then said electric clamp is automatically actuated to shut off the first branch 31a, such as to completely bypass the dialyzing liquid from the element 33, which is thus eliminated from the flow path of the dialyzing fluid at an incorrect temperature. As soon as the temperature level is brought back to the preset range, the electric clamp shuts off the second branch 31b, and the dialyzing liquid flows within the dialyzer element 33.

A very important feature of the machine just described is that all of the elements wherethrough the dialyzing fluid passes are of the "throw-away" type; in other words the suction duct 2, the temperature sensing members 3 and 11, heating tube 4a. suction duct 9, the pumping elements of the peristaltic pump 10, delivery ducts 31 and 32, and obviously, the dialyzer element 33 itself, are utilized but once and discarded after use, and replaced with sterile elements, obviously made of non-toxic materials.

The machine according to this invention operates in the following manner. The dialyzing liquid picked up from the reservoir 1 is passed to the first temperature sensor where the first probe 16 reads the temperature, which in practice will correspond to the temperature of the dialyzing liquid inside the reservoir 1. This reading is very important because the temperature of the dialyzing liquid within the reservoir 1 is not constant, it being continuously recirculated to the reservoir 1 a dialyzing liquid which has already undergone heating, and this causes a continuing variation of the temperature inside the reservoir 1.

The dialyzing liquid is then introduced in the heating tube 4a which, as mentioned above, is made of an electrically conductive material and which, as the current passes therethrough, heats up and transfers heat to the dialyzing liquid to raise it to the desired temperature. At the outlet of the heating tube 4a, a second temperature sensing member 11 is provided which, through the second thermal probe 17, detects the precise temperature of the dialyzing liquid which is to be admitted to the element 33; this reading has two functions: the first is the piloting of the thermal adjusting member 20 that will actuate the heating element in accordance with the temperature differential or gradient sensed at the inlet and outlet of the heating tube 4a; the second function, which is performed by the third thermal probe 18, is that of driving the control assembly 51 which is operative, as mentioned above, to exclude the dialyzer element 33 when the temperature of the dialyzing liquid is not within an acceptable temperature range. For a clearer illustration of the situation, it may be useful to add that for the dialyzing liquid, the thermal adjusting member 20 is generally preset, through the unit or assembly 22, for a preferred temperature of 38° C., whereas the control assembly 51 has a temperature range, generally from 35° to 40° C.

The dialyzing liquid is partly supplied, through the pump 10, to the regenerative cartridge 40, known per se. The rest of the dialyzing liquid is passed, through the dialyzer element 33 if the electric clamp 50 releases the first branch 31a, or bypasses the element 33, as already explained above, if the first branch 31a is blocked and the second branch 31b released, should the liquid be at a different temperature from the one desired or any hazardous conditions arise.

The dialyzing liquid will then be returned to the reservoir 1, wherefrom it is recycled.

A first noteworthy feature of the portable machine for dialysis according to this invention resides in the novel structure of the temperature sensing members; these, in fact, are capable of sensing the temperature in an aseptic manner, since the probes, as illustrated in the foregoing, do not contact the dialyzing liquid but are inserted into the cavities 15 of the cell 12 wherethrough the dialyzing liquid is caused to flow.

Also important, as mentioned above, is that the inlet port 13 be located at a lower level with respect to the outlet port 14, in order to permit a rapid removal of any bubbles formed within the cell 12, which bubbles would cause an alteration of the thermal exchange and consequently inaccurate temperature readings.

It should be further added that the relative capacity of the cell 12 causes the temperature of the dialyzing liquid to remain non-influenced by the thermal exchange with the environment, and above all, the probe is positioned such as not to influence the temperature of the fluid, thereby an extremely accurate reading of the temperature can be obtained.

Another important aspect is that of the heating tube being positioned, as already discussed in the foregoing, such as to define a constantly rising path within it and avoid that a bubble build up in the dialyzing liquid causes poor heat transfer from the heating tube 4a to the dialyzing liquid, and secondarily that local spots are generated whereat owing to an excessive thermal exchange local boiling of the dialyzing liquid is produced, with obvious attendant shortcomings.

It should be added, moreover, that the electrical connection means of the heating tube 4a must be designed specially, the tube being of an electrically conductive material, for preventing localized resistance paths in the secondary circuit of the transformer 8, which paths would affect the current flow, the latter being preset such as to raise to the desired temperature the dialyzing liquid during its flowing through the tube 4a.

Furthermore, it is to be stressed that the temperature sensing members are not directly connected to the heating tube, because otherwise one could obtain false readings, caused by the tube heating up when under current flow.

From the foregoing, it will be apparent that the invention achieves its objects, and in particular attention is drawn to it characteristically comprising throw-away elements that make its utilization extremely simple and practical, there being no sterilization problems with the component parts, which permits the machine described above to be used for home dialyses, with obvious attendant benefits.

Moreover, the control means provided on the machine in no cases admit to the inside of the dialyzer element 33 a dialyzing fluid lacking the desired characteristics of temperature and purity.

The invention as indicated is susceptible to many modifications and variations, all of which are intended to fall within the scope of the instant inventive concept.

Furthermore, all of the details indicated may be replaced by other technically equivalent ones.

In practicing the invention, the materials used, on condition that they are compatible with the particular applicational requirements, and the dimensions and shapes may be any ones to suit the application.

I claim:

1. A portable machine for regenerative dialysis, characterized in that it comprises a reservoir for the dialyzing liquid, a suction duct immersed in said reservoir, a heating element connected to said suction duct, a first element sensing the temperature of the dialyzing liquid interposed between said suction duct and said heating element, a pump with the suction side thereof connected to said heating element, a second element sensing the temperature of the dialyzing liquid interposed between said pump and said heating element, a first and second delivery ducts of said pump opening into said reservoir, a dialyzer element interposed in said first delivery duct, a dialyzing liquid regenerating cartridge interposed in said second delivery duct, a first and second thermal probes respectively associated with said first and second temperature sensing elements, and a temperature adjusting member controlling said heating element and driven by said first and second thermal probes.

2. A portable machine for regenerative dialysis, according to the preceding claim, characterized in that it comprises a preset temperature setting assembly interconnected with said temperature adjusting member.

3. A portable machine for regenerative dialysis, according to claim 1, characterized in that said heating element comprises a transformer and a heating tube serially connected to the secondary of said transformer and made of a non-toxic electrically conductive material wherethrough said dialyzing liquid flows, said temperature adjusting member being located on the primary of said transformer.

4. A portable machine for regenerative dialysis, according to claim 1, characterized in that said first and second sensing elements comprise respectively a substantially cylindrical cell having at one base an inlet port and outlet port diametrically opposite each other, said inlet port being at a lower level than said outlet port, at the opposite base said cell being provided with an outwardly open cylindrical cavity adapted for accomodating said thermal probes.

5. A portable machine for regenerative dialysis, according to claim 1, characterized in that it comprises on said first delivery duct a bifurcation including a first branch, on which is interposed said dialyzer element, and a second branch bypassing said dialyzer element, an electric clamp adapted for closing either said first or said second branch to control said bifurcation.

6. A portable machine for regenerative dialysis, according to claim 5, characterized in that it comprises a control assembly controlling said electric clamp, a temperature range outside whereof said electric clamp closes said first branch leaving said second branch open being presettable in said control assembly, in said temperature range said electric clamp being operative to close said second branch and leave said first branch open, a third thermal probe, accomodated within the cylindrical cavity of said second temperature sensing element driving said control assembly.

7. A portable machine for regenerative dialysis, according to claim 4, characterized in that said heating tube of said heating element has a substantially V-like shape and has at the end an inlet port and outlet port, said heating tube extending in a substantially vertical plane, said inlet port being at a lower level than said outlet port, said tube defining inside it a uniformly rising path.

8. A portable machine for regenerative dialysis, according to claim 1, characterized in that all of the elements wherethrough the dialyzing fluid flows are of the "throw-away" type.

* * * * *